(12) United States Patent
Pai et al.

(10) Patent No.: US 10,589,114 B2
(45) Date of Patent: Mar. 17, 2020

(54) PLASMA THREAD

(71) Applicant: The Board of Regents for Oklahoma State University, Stillwater, OK (US)

(72) Inventors: Kedar K. Pai, Stillwater, OK (US); Jamey D. Jacob, Stillwater, OK (US); Chris Timmons, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 191 days.

(21) Appl. No.: 15/566,305

(22) PCT Filed: Apr. 14, 2016

(86) PCT No.: PCT/US2016/027595
§ 371 (c)(1),
(2) Date: Oct. 13, 2017

(87) PCT Pub. No.: WO2016/168502
PCT Pub. Date: Oct. 20, 2016

(65) Prior Publication Data
US 2018/0099149 A1 Apr. 12, 2018

Related U.S. Application Data

(60) Provisional application No. 62/147,055, filed on Apr. 14, 2015.

(51) Int. Cl.
*A61N 1/44* (2006.01)
*A61L 2/14* (2006.01)
(Continued)

(52) U.S. Cl.
CPC .......... *A61N 1/44* (2013.01); *A61B 17/06166* (2013.01); *A61F 13/00008* (2013.01);
(Continued)

(58) Field of Classification Search
CPC ..... A61B 17/06166; A61B 2017/00889; A61F 13/00008; A61L 2202/24; A61L 2/14;
(Continued)

(56) References Cited

U.S. PATENT DOCUMENTS 4,475,006 A 10/1984 Olyphant
5,326,530 A 7/1994 Bridges
(Continued)

FOREIGN PATENT DOCUMENTS

EP 0997926 A2 5/2000
GB 2449707 A 12/2008
(Continued)

OTHER PUBLICATIONS

EP16780773, Supplementary European Search Report, dated Dec. 10, 2018.
(Continued)

*Primary Examiner* — Imani N Hayman
(74) *Attorney, Agent, or Firm* — Crowe & Dunlevy; Terry L. Watt

(57) ABSTRACT

There is provided herein, according to an embodiment, a plasma thread application of dielectric barrier discharge, which incorporates the effectiveness of plasma in sterilization and the flexibility of thread like structure and has the malleability to be formed into any apparel design. The design of one embodiment uses a dielectric coated/insulated wire in the range of 30 to 40 awg based on the application in question. It can be used as sutures or can be woven into a material for countless bandage-like applications. The ready availability of medically approved dielectric materials is conducive to the manufacture of the same.

6 Claims, 5 Drawing Sheets

(51) Int. Cl.
*A61B 17/06* (2006.01)
*A61F 13/00* (2006.01)
*A61M 25/00* (2006.01)
*H05H 1/24* (2006.01)
*A61B 17/00* (2006.01)

(52) U.S. Cl.
CPC .......... *A61L 2/14* (2013.01); *A61M 25/0043* (2013.01); *H05H 1/2406* (2013.01); *A61B 2017/00889* (2013.01); *A61L 2202/24* (2013.01); *A61M 2025/0019* (2013.01); *H05H 2001/2412* (2013.01); *H05H 2001/2418* (2013.01); *H05H 2001/2431* (2013.01); *H05H 2245/122* (2013.01)

(58) Field of Classification Search
CPC ...... A61M 2025/0019; A61M 25/0043; A61N 1/44; H05H 1/2406; H05H 2001/2412; H05H 2001/2418; H05H 2001/2431; H05H 2245/122
See application file for complete search history.

(56) References Cited

U.S. PATENT DOCUMENTS

| | | | |
|---|---|---|---|
| 6,455,014 | B1 | 9/2002 | Hammerstrom et al. |
| 7,869,556 | B2 | 1/2011 | Morfill et al. |
| 8,362,699 | B2 | 1/2013 | Eden et al. |
| 2003/0072675 | A1 | 4/2003 | Takeda et al. |
| 2004/0022907 | A1 | 2/2004 | Mielnik et al. |
| 2008/0245478 | A1 | 10/2008 | Hotta |
| 2009/0209958 | A1 | 8/2009 | Davison et al. |
| 2009/0281569 | A1 | 11/2009 | Alghamdi |
| 2011/0116967 | A1 | 5/2011 | Roy et al. |
| 2012/0039747 | A1 | 2/2012 | Morfill et al. |
| 2012/0046597 | A1 | 2/2012 | Morfill et al. |
| 2012/0259270 | A1 | 10/2012 | Wandke et al. |
| 2012/0271225 | A1 | 10/2012 | Stieber et al. |
| 2013/0022514 | A1 | 1/2013 | Morfill et al. |
| 2013/0053762 | A1 | 2/2013 | Rontal et al. |
| 2013/0226073 | A1 | 8/2013 | Kummerfeld et al. |
| 2013/0345620 | A1 | 12/2013 | Zemel et al. |
| 2015/0008825 | A1 | 1/2015 | Eden et al. |
| 2015/0088234 | A1 | 3/2015 | Weltmann et al. |

FOREIGN PATENT DOCUMENTS

| | | |
|---|---|---|
| JP | 2012104486 A | 5/2012 |
| WO | 2004099490 A1 | 11/2004 |

OTHER PUBLICATIONS

Birmingham, "Mechanisms of Bacterial Spore Deactivation Using Ambient Pressure Nonthermal Discharges", Aug. 2004, pp. 1526-1531, vol. 32, No. 4, Publisher: IEE Transactions on Plasma Science, Published in: US.

Price et al, "Plasma Sheets and Cylinders Generated from Aluminimum Wire Fabric", Aug. 2008, pp. 1252-1253, vol. 36, No. R, Publisher: IEEE Transactions on Plasma Science, Published in: US.

PCT/US2016/027595, International Search Report and Written Opinion; Title: Plasma Thread; Applicant: The Board of Regents for Oklahoma State University; dated Aug. 31, 2016.

Fluid flow

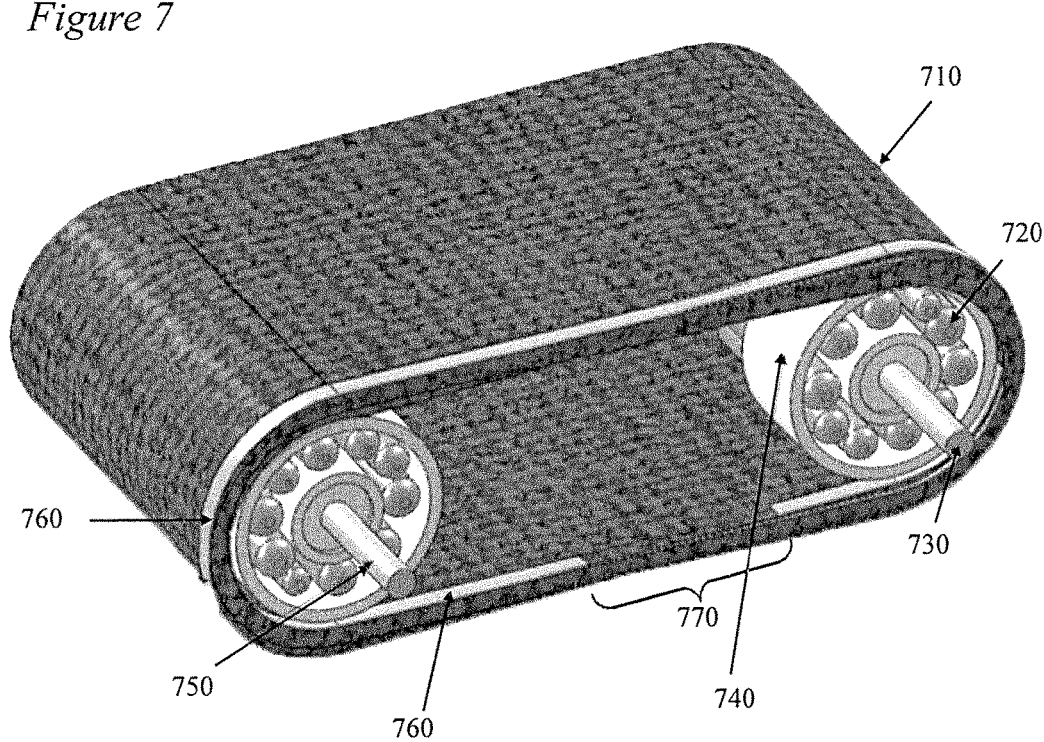
*Figure 7*
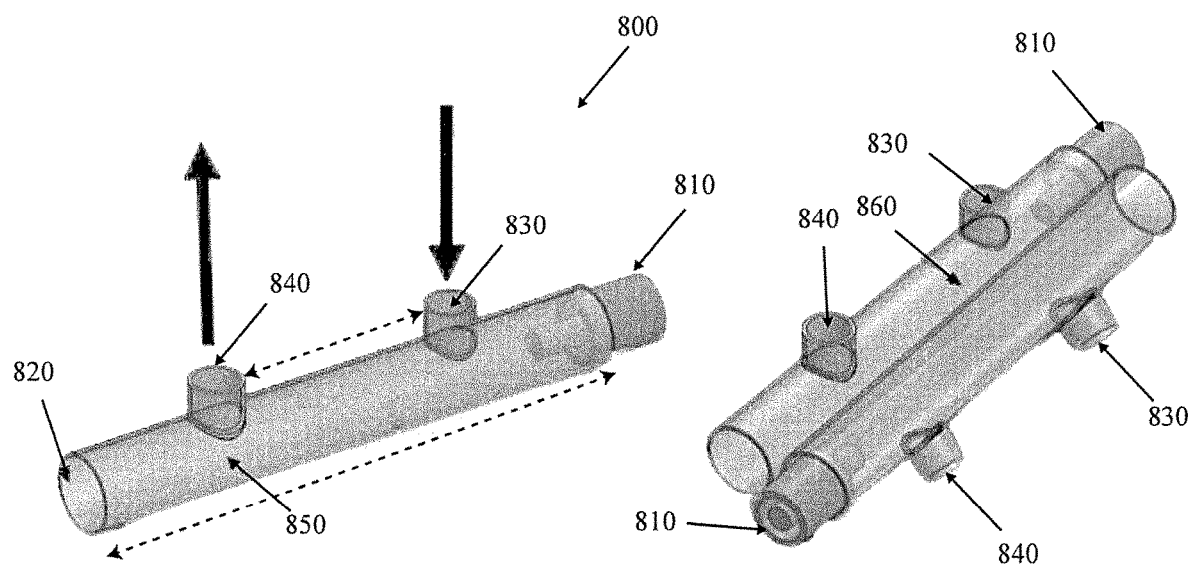
*Figure 8A*  *Figure 8B*

PLASMA THREAD

CROSS REFERENCE TO RELATED APPLICATIONS

This application claims the benefit of U.S. Provisional Patent Application Ser. No. 62/147,055 filed on Apr. 14, 2015, and incorporates said provisional application by reference into this document as if fully set out at this point.

TECHNICAL FIELD

This disclosure relates generally to a sterilization and healing and, more particularly, to a plasma thread which is a sterilization and healing device that utilizes the principle of dielectric barrier discharge plasma actuator to generate plasma using linear tube like electrode arrays.

BACKGROUND

Taking into account chronic wounds and hospital acquired infections which amount to over 6.5 million occurrences per year, there is a clear economic and medical incentive to making the wound healing process faster and less susceptible to infection. Diabetics are especially prone to chronic wounds often contract deadly infections on their skin and tissues due to higher glucose levels and an impaired immune response to different pathogens.

Cold atmospheric plasma can be used to decontaminate most surfaces without damaging the material of the surface being treated. Since its effects are superficial and not bulk it's easy to implement and control. Limited doses on the order of minutes are enough to generate a considerable disinfection/sterilization effect. In recent years applications of plasma for wound disinfection and healing have received a lot of attention. Multiple researchers have shown the beneficial effects of plasma based tools like the plasma needle and the plasma torch for wound and instrument sterilization.

Plasma devices based on their ability to use atmospheric air and produce reactive nitrogen and oxygen species along with various products like ozone and nitric oxide, can not only help decontaminate the wound of any pathogens but also accelerate wound healing without damaging the surrounding healthy tissue.

Dielectric barrier discharge (DBD) is a type plasma generation process wherein plasma is created due to the accumulation of charge on one side of a dielectric medium between two electrodes. The dielectric medium does not permit the passage of charge which, in turn, develops to oppose the applied electric field until the field is balanced. This migration of charge and generation of ions in the process continue till the charge stops growing and the discharge extinguishes. This process of charge accumulation in the form of plasma is a very ephemeral process and the discharge time span is on the order of seconds. The prior art teaches a mesh made of a plasma wire where two wires are placed orthogonally, thus restricting the plasma formation to the junctions between two wires of opposite polarity.

Others have proposed a design for internal treatment in the form of a probe or a balloon and a cuff for external exposure. The design uses elastic materials but this approach has the risk of cracking metallic contacts as these might not be stretchable. Also, one of the electrodes needs to be grounded.

All these designs also restrict the ability of the plasma generating surface to be exposed to water or liquids, as the exposed electrode may be corroded or damaged.

Heretofore, as is well known in the wound healing and infection prevention arts there has been a need for an invention that is designed to overcome the disadvantages of prior art approaches. Accordingly it should now be recognized, as was recognized by the present inventors, that there exists, and has existed for some time, a very real need for a system that would address and solve the above described and other problems.

Before proceeding to a description of the present invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

According to an embodiment, the plasma thread application of dielectric barrier discharge, which incorporates the effectiveness of plasma in sterilization and the flexibility of thread like structure, has the malleability to be formed into any apparel design. One embodiment of a design uses a dielectric coated/insulated wire in the range of about 30 to 40 awg (American Wire Gage) based on the application in question, i.e., it can be thicker or thinner depending on the needs of the particular usage. It can be used as sutures to close a wound in a human or animal, or can be woven into a material for countless bandage-like applications. The ready availability of medically approved dielectric materials is conducive to the manufacture of the same.

The plasma thread application of dielectric barrier discharge, which incorporates the effectiveness of plasma in sterilization and the flexibility of thread like structure, has the malleability to be formed into any apparel design. The design uses a dielectric coated/insulated wire in, but not restricted, to the range of 30 to 40 awg based on the application under consideration.

This embodiment can be used as sutures or can be woven into a material for countless bandages like applications. The availability of medically approved dielectric materials helps the easy manufacture of the same. The plasma thread design of one embodiment consists of two designs namely a DBD (Dielectric Barrier Discharge) configuration using two electrodes braided or intertwined together as shown in FIG. 1 and the second configuration which is the FE-DBD (Floating Electrode-Dielectric Barrier Discharge) type as shown in FIG. 2. This design uses the living tissue as the grounded electrode.

These designs can be scaled up by changing the wire diameter. The smaller diameters are however beneficial as they reduce the formation of deep crevices between two consecutive loops of these threads. The plasma thread can be sown into countless designs like patches and bands for in the field as well as military applications for health care.

An embodiment of the thread design described herein is both user-friendly and not damaging to healthy tissue as has been shown in past literatures. The heating problem is mitigated using pulsed cycles.

An embodiment taught herein does not suffer from various disadvantages of the prior art because, among other reasons, the tubes used are easily stretchable and the fluid inside changes its volume to accommodate this change making it ideal for stretchable bandages. Additionally, a design taught does not need a grounded electrode and can use different polarities so as to generate various species of ions and radicals to treat a particular infection or injury.

Also, various embodiments mitigate the damage that can occur when exposed to to fluids and the like through the use fluid based electrodes and tubing which may have microgrooves the form air pockets preventing total submersion.

According to one embodiment, there is provided a plasma generating thread, comprising: a first strand of a conductive material encased in dielectric material; and, a second strand of said conductive material insulated from said first strand of conductive material and intertwined with said first strand of conductive material, wherein said second strand of said conductive material is encased in said dielectric material, wherein said first and second strand operate as a plasma generating source along their entire length when subject to a plasma inducing voltage.

In another embodiment, there is taught herein a method of treating a wound, wherein is provided a plasma generating thread, comprising the steps of: closing the wound using said plasma generating thread; applying power to said plasma generating thread, thereby generating plasma using said generating thread while said thread is present as a suture in the wound and closing it.

Another embodiment is a self-sterilizing catheter, comprising: a wall of a dielectric material defining a hollow catheter body; and, a plurality of spaced apart positive electrodes alternating with a plurality of spaced apart negative electrodes distributed within said wall.

Another embodiment teaches a method of treating an open wound, comprising the steps of: accessing a plasma generating thread comprising a first strand of a conductive material encased in dielectric material, and a second strand of said conductive material insulated from said first strand of conductive material and intertwined with said first strand of conductive material, wherein said second strand of said conductive material is encased in said dielectric material; closing the wound using said plasma generating thread; and, applying power to said plasma generating thread, thereby generating plasma using said generating thread while said thread is present in the wound; and, repeating step (c) at plurality of spaced apart times while the wound is healing.

An apparatus for treating a subject with plasma radicles, comprising: a first tubular member constructed of a dielectric material and having a first interior, said first tubular member containing a positive electrode in said first interior, said first tubular member having a first inlet and a first outlet for receiving and discharging fluid from an interior of said first tubular member; and, a second tubular member constructed of said dielectric material having a second interior and situated proximate to said first tubular member, said second tubular member containing a negative electrode in said second interior, said second tubular member having a second inlet and a second outlet for receiving and discharging fluid from an interior of said second tubular member.

Another embodiment takes the form of an apparatus for treating a subject with plasma radicles, comprising: a Peltier module, a first tubular member constructed of a dielectric material and having a first interior, said first tubular member containing a positive electrode in said first interior, said first tubular member electrode being in thermal communication with said Peltier module; and, a second tubular member constructed of said dielectric material having a second interior and situated proximate to said first tubular member, said second tubular member containing a negative electrode in said second interior, said second tubular member being in thermal communication with said Peltier module.

The foregoing has outlined in broad terms some of the more important features of the invention disclosed herein so that the detailed description that follows may be more clearly understood, and so that the contribution of the instant inventors to the art may be better appreciated. The instant invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

These and further aspects of the invention are described in detail in the following examples and accompanying drawings.

FIG. 7 contains a schematic diagram of how a mesh embodiment might be used to form a belt on a conveyor.

FIGS. 8A and 8B illustrate an embodiment of a tube-type plasma thread in which fluid is can be circulated to provide cooling to the system.

DETAILED DESCRIPTION

Figure 1:
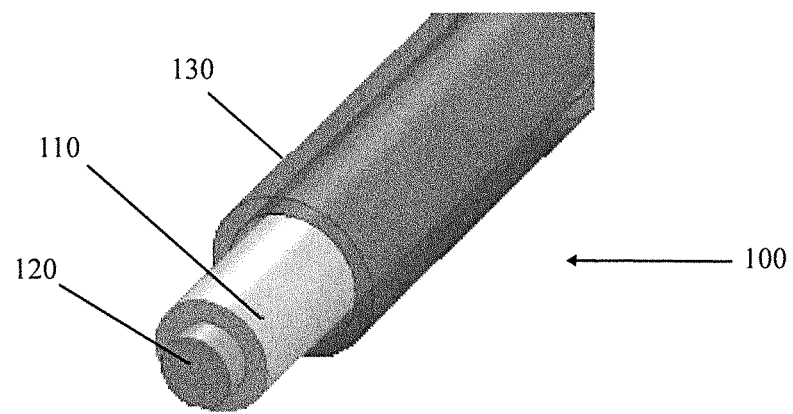
FIG. 1 contains a schematic of an embodiment of a plasma thread (single thread) FE-DBD design.

While this invention is susceptible of embodiment in many different forms, there is shown in the drawings, and will herein be described hereinafter in detail, some specific embodiments of the instant invention. It should be understood, however, that the present disclosure is to be considered an exemplification of the principles of the invention and is not intended to limit the invention to the specific embodiments or algorithms so described.

Figure 5:
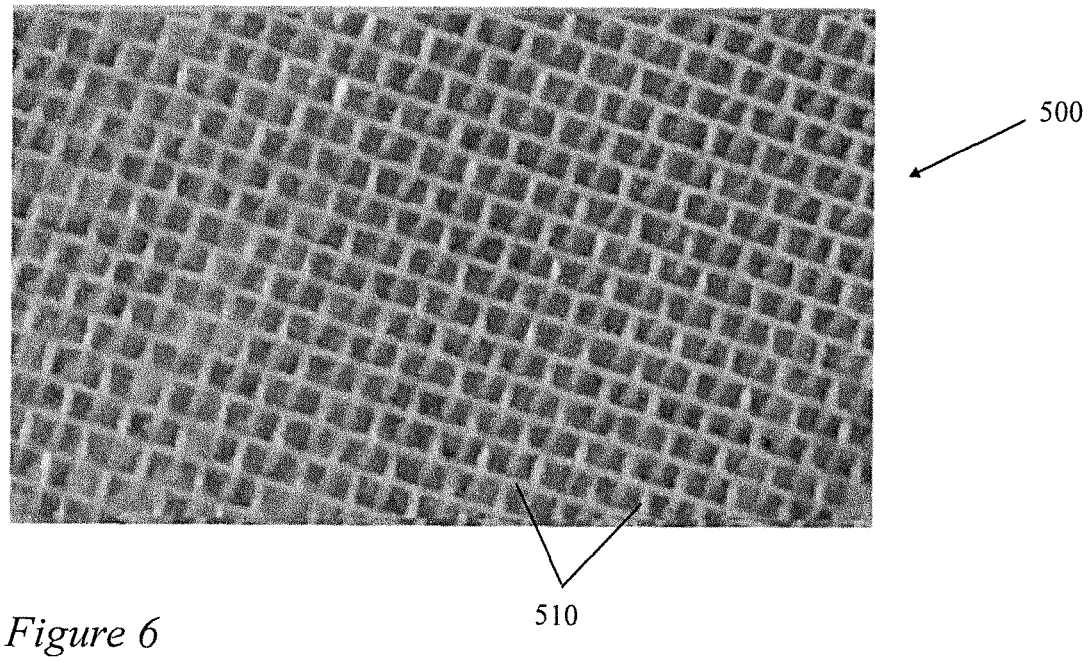
FIG. 5 contains an illustration of an embodiment of a braided mesh-type plasma generating system.

According to an embodiment, plasma thread has the malleability to be formed into any apparel or other similar design and can thereafter generate a dielectric barrier discharge, which incorporates the effectiveness of plasma in sterilization and the flexibility of thread-like structure. One embodiment uses a dielectric coated/insulated wire in the range of 30 to 40 awg which might be chosen based on the application in question. Generally speaking, the gage of wire that is used will usually be comparable in diameter to that of suture size that would be used in that application (e.g., suture sizes of 7 to 11-0 according to the USP definition), although gages outside that range can be useful. This embodiment can be used as sutures or can be woven into a material for bandages or similar applications (e.g., as illustrated in FIG. 5). The availability of medically approved dielectric materials helps makes decisions regarding the manufacture of the same more tractable.

Various embodiments of the thread design are both user-friendly and not damaging to healthy tissue. The heating problem which is often encountered with plasma-generating devices can be mitigated using pulsed cycles (with am on/off percentage dependent on effect desired) or circulation of water or other coolants to provide a cooling effect to the wound. Even with 800 milliseconds on and 300 milliseconds off the heating effect can be decreased considerably, thus increasing the electrode life spans and reducing the risk of burns. The high voltage frequency for the power may range from Hz to k Hz and the input to the thread could be on the order of kilo volts (preferably 2 and above). For example, one way to choose the voltage would be to choose a voltage sufficient to match the breakdown voltage of the dielectric material. While the current will typically be on the order of microamperes (but preferably lower than 100 milliamps) in some embodiments, which mitigates the risk of any shock or other issues such as burns.

One advantage of the foregoing is that when this embodiment is used in place of, or as a supplement to, conventional suture thread, the instant plasma generator can be left in place while the wound heals, thereby making it possible to periodically sterilize the wound internally and externally again during the healing process. For example, the suture/generating thread might be activated at spaced apart intervals of 1 hour, 12 hours, 1 day, multiple days, etc. The exact time spacing would typically need to be determined on a case by case basis depending on the severity of the infection, the location in the body, the depth of the wound, etc. After the wound has healed sufficiently, the plasma threads would be removed as would any non-dissolving suture.

Additionally, although the braided pair configuration is a preferred configuration for this particular application, two parallel strands that are in close proximity throughout their generating length could also be used, in which case the plasma radicles will be generated by coplanar discharge. Additionally, two parallel conductors may be placed placed apart in a dielectric producing a single strand generating plasma that generates plasma on its surface due to co-planar discharge. The dielectric in this case can have cross-sectional shapes different from linear, e.g., such as cylindrical, convex, or concave, etc.

Figure 2A:
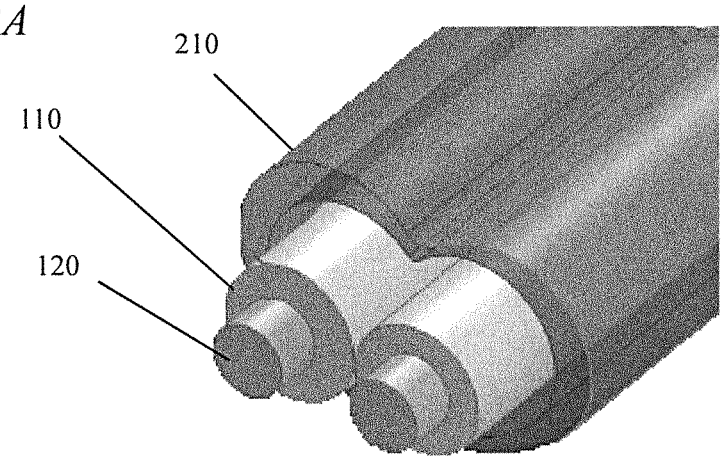
FIGS. 2A and 2B contain a schematic illustration of an embodiment of a plasma thread (braided) DBD design.

Turning first to FIGS. 1 and 2, two embodiments of a plasma thread design include a DBD (Dielectric Barrier Discharge) configuration using two electrodes braided together are shown in FIG. 1 and a second configuration which is the FE-DBD (Floating Electrode-Dielectric Barrier Discharge) type as shown in FIG. 2A. This design uses the living tissue as the grounded electrode. These designs can be scaled up or down by changing the wire diameter. Smaller diameters are beneficial in some cases, and may be preferred at times because they tend to reduce the formation of deep crevices between two consecutive loops of these threads. The plasma thread can be sown and/or woven into countless designs such as patches, bands, meshes, etc., for use in the field as well as military applications for health care.

In the variation of FIG. 1, the thread 100 contains at its core a conductor 120 which will be an electrode (e.g., a metal electrode such as copper, silver, aluminum, etc., or any other solid or liquid conductive material) which is surrounded by a dielectric 110 such as polyimides, polymers, resins, Teflon®, LDPE (low density polyethylene), plastic, etc. and 130 is a schematic representation of the plasma field that would be generated by this embodiment when it is powered.

Figure 2B:
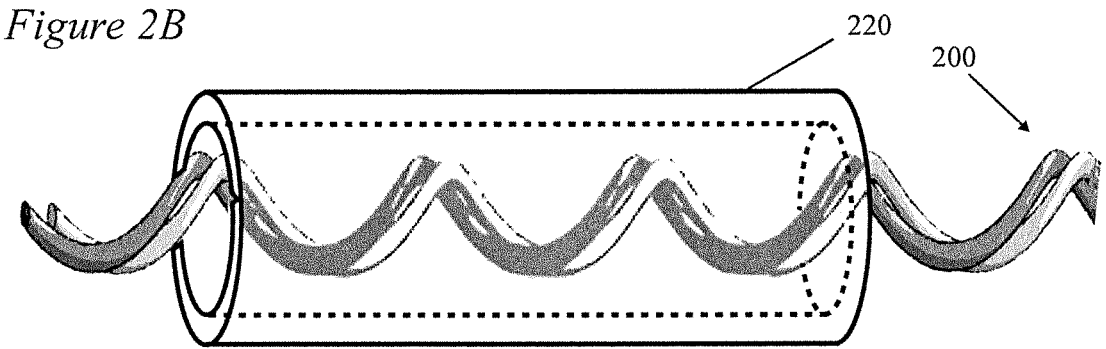
Figure 4:
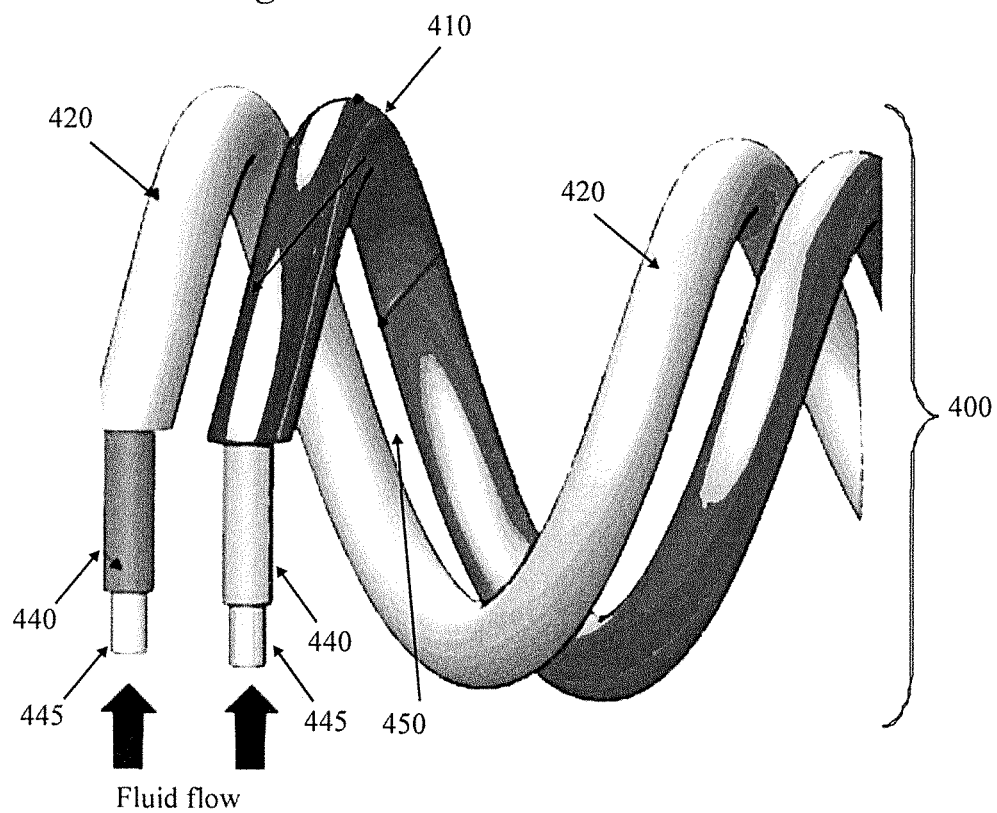
FIG. 4 contains a schematic view of an embodiment which provides internal cooling via a circulating fluid arrangement.

According to an embodiment there is provided a plasma generating apparatus which is formed by braiding together, for example, two or more threads 100 which are wires coated or insulated by a dielectric (e.g., FIGS. 2B and 4). In FIG. 2B, the embodiment 200 has been braided and inserted into a tube 220. One way this embodiment might be utilized would be to apply power and then force air through the tube 220 so as to transport the plasma generated radicles out of the tube 220 and onto a surface or into a container. By way of example, the container might contain a solid, powder, or liquid that is to be decontaminated. The radicles could be blown on or bubbled through the contents of the container. In the later case, the air flow can help better distribute the plasma decontamination effect while agitating the powder into which it is blown. Similarly, this design could also be used to bubble plasma generated species into chemicals or water to produce a similar result.

A braided embodiment could also be made, as an example, by braiding two or more pipes or tubes coated with a dielectric material such as Teflon® or LDPE, and which are filed with an electrolyte or conductive fluid like salt water. These tubes then can be powered by introducing a conductive lead from the power source at one end (e.g., FIGS. 8A and 8B). In FIGS. 8A and 8B, circulating fluid (e.g., salt water) will be introduced into the dielectric tube 850 via an intake portal (inlet 830) and expelled via outlet 840. In the embodiment of FIG. 8A, the end 820 of the tube is closed which would be a way to seal the terminus of the tube 850. In FIG. 8B, the ends are open which would be the case where a connection to another/similar unit is desired. In this figure, a power connector 810 (in H.V.) is provided to allow current to be applied to the contents of tube 800. Inn some embodiments this will be while the fluid which occupies the interior of the tube 850 is circulated.

The fluid could be stationary (e.g., by sealing one end of the plasma thread) so that it is cooled by conduction, or it could be part of a circulating system which can be configured to aid in cooling. The power may be provided through a wall supply or battery operated using a lithium ion or solar or other portable power source, etc.

Not shown in this figure is a pump or other device for urging fluid into inlet 830. In some embodiments this will be a diaphragm pump (which would be able to operate while power was supplied to the electrolyte). Alternatively, a wide variety of different pumps could be used if, for example, the pulse/charge on the fluid was not active when the pump was cycling. That is, the pulse to the electrodes 810 would alternate with power to the pumping unit.

FIG. 4 provides another example of a cooling embodiment. In that figure, cooled fluid is circulated into hollow tubes 445 which might be encased, for example, within conductive metal tubing (e.g., copper) to provide connectivity with a power source. In the embodiment of this figure, the negative/ground tube is element 420 and the positive/ground tube is element 410. Plasma will be generated within the gaps between tubes 450. Additionally, and not shown, will be a pump or other mechanism for forcing the fluid into hollow tubes 445 (e.g., made of plastic) and a heat exchanger or other mechanism for cooling the fluid that exists from the tubes before it is cycled again back into the apparatus 400. The dielectric in this case might be Teflon® or polyurethane. Of course, the hollow tubes 445 that line the metal tubing could easily be eliminated if such were desired.

A related design may be made by coating the inside of the tube 445 with conductive paint such as colloidal silver. This design can further provide cooling to the wound or any such application that requires cooling by an air stream through this tube in a similar fashion to the water cooled system. The above designs can hence be fashioned as patches, jackets or bandages (e.g., for use with burn victims).

Figure 9:
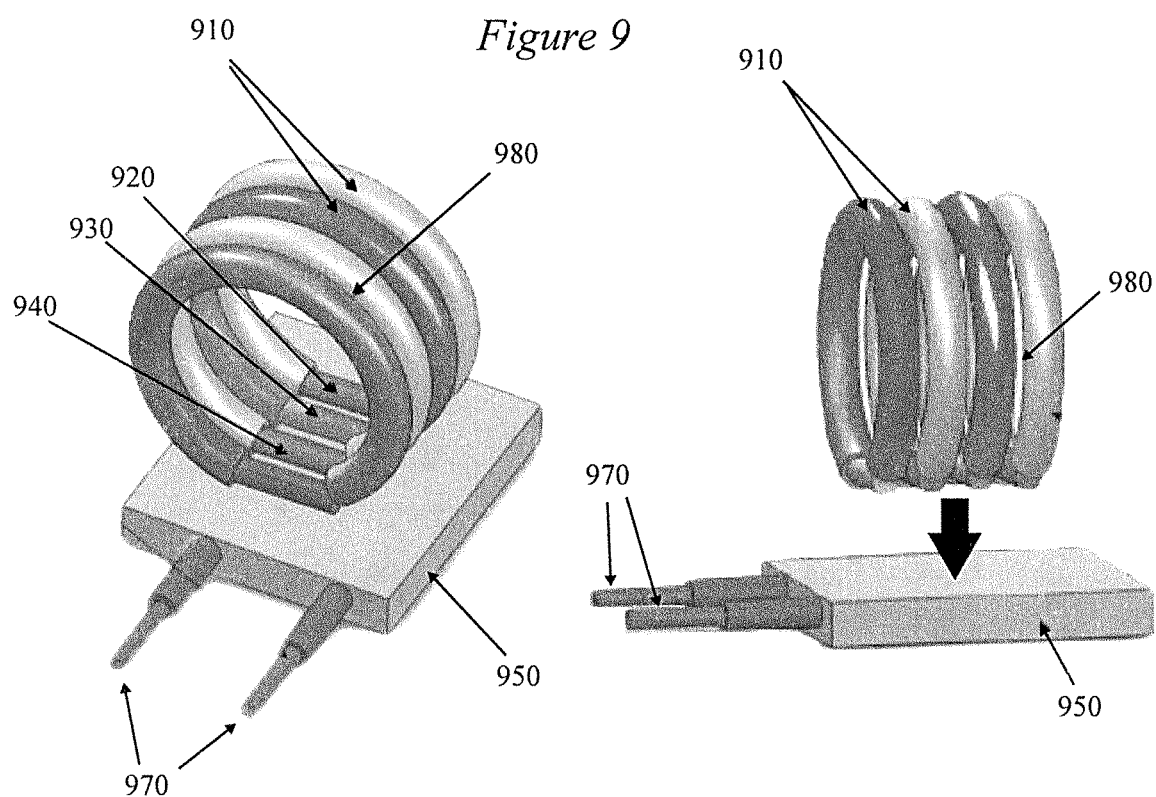
FIG. 9 contains a cooling tube-type embodiment using heat tubes filled with liquid or cooling gel that can provide cooling to injuries that would benefit from that effect.
Figure 10:
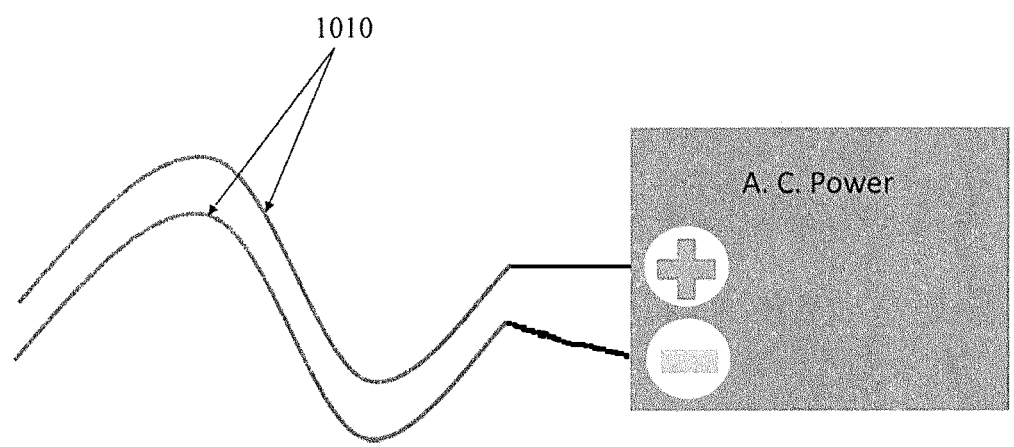
FIG. 10 contains a schematic illustration of a system suitable for use with an embodiment.

Another design, as shown in FIG. 9, can be configured with heat tubes filled with liquid (e.g., a conductive liquid mixed with glycerol, etc.) or cooling gel that with the help of a Peltier unit or other methodology, is kept cool, thus allowing for cooling of injuries, for example burn wounds. In this figure, the dielectric cladding 910 has been chosen to be the dielectric PTFE or PU, although many alternative choices could be made by those of ordinary skill in the art. A Peltier unit 950 with leads 970 is in thermal communication with the electrodes 920/930/940, the Peltier unit 950 providing cooling to this embodiment. Noted in this figure are positive/ground 920 element and negative/ground 930 which will be used to generate plasma radicles. Exposed heat tubes of copper 940 expedite the heat transfer between the Peltier unit 950 and the plasma tubes. As might be expected, plasma will be generated in the gaps 980 between the positive 920 and negative 930 rings when power is supplied to the unit.

The heat tubes in this embodiment could be made of metal such as copper, although many other materials are heat conductive and could be used in the place of copper. Tubes of opposite polarity 920/930/940 are placed alternately and covered by dielectric such as polytetrafluoroethylene (PTFE) or polyurethane (PU). The ends exposed to the Peltier are cooled thus cooling the entire tube by conduction and convection.

Continuing with the present example, to avoid arcing or electromagnetic effects the plasma and the cooling unit may be pulsed alternately so that both are not on simultaneously. The individual tubes make for ease of replacement. Alternately the tube may be continuous as well in the form of a spiral, where in the liquid may be circulated with the assistance of a pump so as to have a continuous cooling effect by running fluid. The tubes may be but are not restricted to just Teflon with fluid inside or copper tubes with Teflon cladding with air or fluid flowing inside as shown in FIG. 4.

Continuing with the example of FIG. 4, these designs could be used to create jackets for both patients as well as applications such as tissue conservation in a sterile environment. The inventive thread (both wire type and tube type) can be used to make but not restricted to bandages, braces, cuffs or bands (FIG. 3), jackets, belts and much more for various applications like but not restricted to sterilization and wound care.

Embodiments of the plasma thread taught herein will be configurable into form factors such as braided wires (FIGS. 2B and 4) or a (FIG. 5). The mesh embodiment of FIG. 5 could be made using various braid designs such as a plain weave or a dutch weave or even weaving or knitting it on a substrate material by using methods from embroidering designs. In FIG. 5, each of the strands 510 is a braided wire embodiment of the sort taught herein. An alternative embodiment would be to form the mesh from multiple pairs of parallel electrodes, each covered with dielectric material (i.e., a coplanar discharge plasma generator).

The applications are not limited to sutures to close wounds or just patches for injuries. Embodiments may be used for topical and intrinsic application. For topical applications an embodiment can be used to treat infections such as those caused by staphylococcus and *pseudomonas* or fungal infections and skin conditions as needed due to the presence of reactive oxygen and nitrogen species. For intrinsic applications the thread may be used for probes in ear canals or cavities where fine tools and precision is needed. It can even be used to make self-sterilizing catheters.

Figure 6:
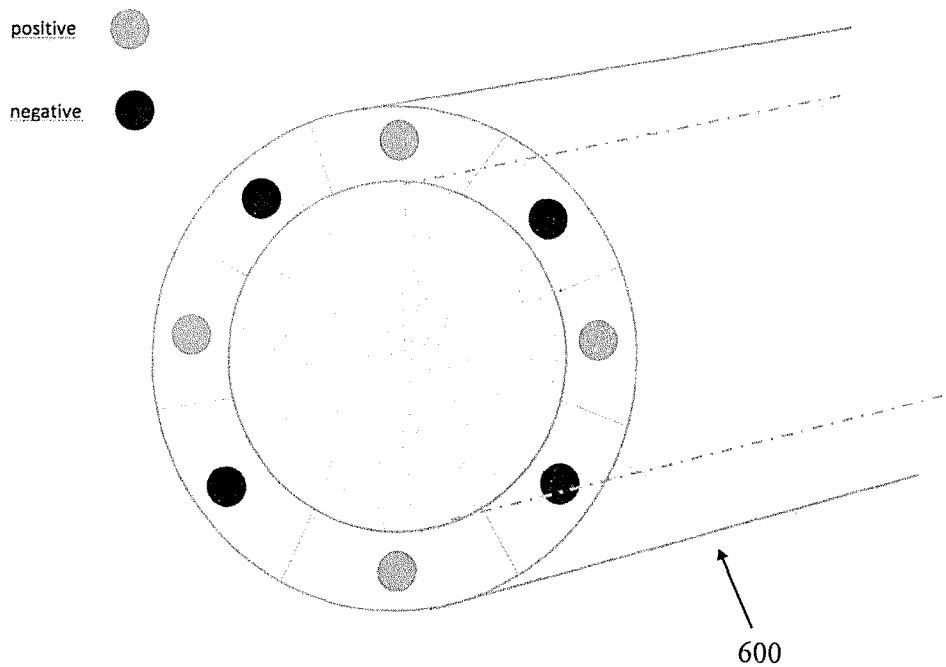
FIG. 6 contains a schematic diagram of an embodiment that might be used with a catheter.

According to the self-sterilizing catheter embodiment of FIG. 6, positive and negative electrodes are separated by the catheter material and are arranged longitudinally within the body of the catheter. As is indicated in the example of this figure they will be placed uniformly about the perimeter of the catheter. Of course, other arrangements might have the electrodes spaced apart but oriented circumferentially. Those of ordinary skill in the art will recognize how this might be readily done according to the teachings presented herein. A catheter could also be devised by placing the electrodes in a tight woven mesh around or inside the catheter or even using coplanar discharge like orientation.

Additionally, an embodiment of the plasma thread could be made into a mesh for air treatment and even powder treatment. It can be made into sleeves for tools such as catheters and scopes like the endoscope both for outer an inner surface sterilization.

Military Care

In the field countless injuries occur every day with no immediate access to sterilization. This applies both to the sterilization of instruments as well as sterilization of the wound itself. Countless soldiers and others in locations remote from medical centers have contracted infections such as tetanus due to improper wound care. Plasma thread sutures and bands are ideally adapted to use in remote locations. The plasma bands or sutures can be used on the wounds and left in place after bleeding has stopped. A portable control unit/power supply connected to the same can be used to switch on and off intermittently to continuously sterilize the wound and promote clotting and wound healing. Some embodiments will include a timer circuit which handles the switching. Since the circuit can be powered from a battery it is portable and mobile.

Figure 3:
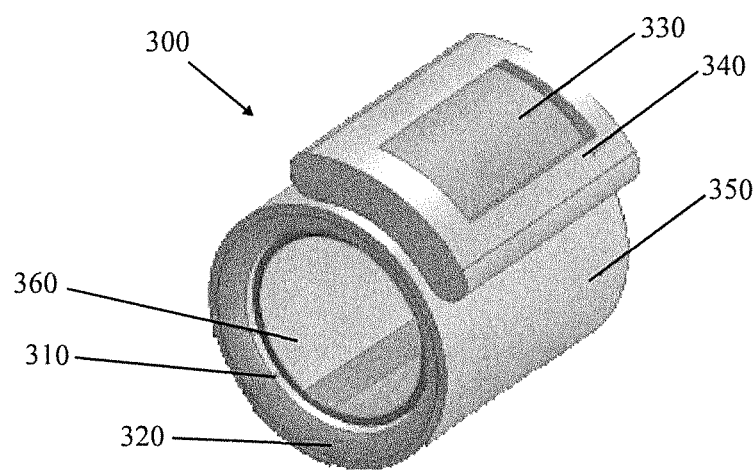
FIG. 3 contains a schematic of an embodiment of a plasma band.

FIG. 3 contains a schematic of an embodiment of a plasma band (e.g., a bracelet) which is designed to surround, for example, a patient's limb. In this arrangement, braided electrodes (e.g., the mesh embodiment of FIG. 5) might be used on the interior of the band in order to generate plasma. More specifically, in this figure braided electrodes 310 are distributed about the inner wall of the cylindrical bracelet 300. The electrodes 310 will be encased within a soft stretchable substrate 320 and an exterior shell of scratch-proof material 350. In some embodiments, a control unit 340 will be configured with an LED display 330 to control the operation of the unit 300. Upon activation, plasma 360 will be generated within the band 300 which will tend to focus the plasma on the wound encircled by the bracelet 300.

A probe made from an embodiment can be used to disinfect various infections such as ear infections (e.g., of the sort seen in dogs) by *pseudomonas* and other infections such as fungal and staphylococcus. The braided embodiment is versatile in that it can be developed to have spiral or any other type of structures if a more rigid wire is used, decreasing its flexibility and increasing its structural integrity. This can even help make spring type structures so as to avoid pressure on tissues such as the tympanic membrane when treating the same. A conventional linear probe may pierce the membrane causing damage. A structure similar to that in FIG. 4 can help mitigate the risk of damage to the patient.

An embodiment of the design can also use a hollow tube or catheter that is filled with an electrolyte such as saline water that has the ability to act as a conductor. This design with the help of circulating liquid can be used to treat wounds resulting from burns as they can be used to both disinfect as well as cool the same (provide a cooling effect).

FIG. 5 shows a mesh embodiment which can be used as a part of the filtration process, wherein powders may be passed through several layers of such a mesh or several times over in order to decontaminate it. This allows not only for a close contact decontamination process as the powder is in direct contact with the plasma, but also this setup can be easily integrated into the current instrumentation used for filtering out clumps formed in the powders. A shaking motion maybe used to break lose any settled powder on the surface of the mesh. The mesh can also be used for treatment of powders or surface by assistance of an additional gas flow including air. The gas is either passed in the gap with the article to be sterilized placed below or on the two electrodes, or using gas flow, the species generated are transported to the site of required microbial inactivation. Also, if the indirect mode of activation is employed the charged particles and UV mostly do not aid in the decontamination process.

The braided wire used to make this mesh allows more versatility in pore size and uniform plasma generation that is not restricted to junctions—for liquids or solids (powders, seeds, grains, granular objects needing bulk sterilization). The woven mesh can be used as a grate for air filtration as well as disinfection by incorporating various weave patterns to change pore size. Air and other powders can also be filtered by using the tread inside a tube by lining the walls of the same or by having the tread concentrically placed along the axis of the tube such as shown in FIG. 9.

In some embodiments, the plasma thread, which might be of the same design as that used to make the braided wire, is placed inside a tube. Air may be blown through the tube so as to assist in the transport of plasma generated radicles into the container housing the powders resulting in both decontamination and mixing More particularly, the design of wires used to make a mesh is not restricted to this form factor. For example, it can be made into a long thread like structure placed axially inside a plastic hose or pipe and air may be blown through this pipe thus carrying the plasma generated species to the container housing the powder. This can help better distribute the plasma decontamination effect while agitating the powder. This design can be used to not just decontaminate powders but also used to bubble plasma generated species into chemicals or water to get similar effects.

This versatile design makes the mesh design ideal for incorporation into sieves and meshes for powder treatment which are currently being decontaminated only through gamma irradiation or heating which damages these powders or their chemical composition in general. Even with these methods available, a wide variety of bacterial contaminants have been isolated from spices and seasonings but two bacterial pathogens stand out in terms of isolation frequency: *Salmonella* and *Bacillus*. *Salmonella enterica* subspecies *enterica* is a human pathogenic, Gram-negative, non-spore-forming bacterium that is well known for its ability to survive for extended periods of time in harsh environments, especially low-moisture environments common to dried spices. In the last 20 years in the United States, *Salmonella* was identified as the causative agent in 71% (10/14) of reported foodborne illness outbreaks involving spices, was the cause of 95% of the food recalls involving spices (Vij et al., 2006), and is yearly the most common contaminant of the "spices and seasonings" category of the DA RFR. Cold plasma according to an embodiment can offer a solution to these sorts of problems by using the mesh as a sieve with multiple passes (if necessary) of the powders through a setup of multiple layers of meshes placed in a stack.

A mesh embodiment can also be utilized as the material that comprises the moving surface of a conveyor belt. As is generally indicated in FIG. 7, the belt 710 utilizes ball bearings 720 or a brush like contact to connect the power to the moving mesh. The connectors 750/730 can be located on either side (or end) of the conveyor so as to avoid arcing. The ball bearing setup can be made for example as shown in but not restricted to the design in FIG. 7. In this figure, also provided is a metal strip 760 which can be used to communicate power to the mesh. The power can be connected on opposite sides of the conveyor along the axis of the spindle or at different points along the conveyor setup. The design can be inverted, wherein the plasma can be generated above the conveyor close to its surface and a thin layer of powders or any other substance can be treated easily, without the plasma being generated on a moving surface. A gap 770 has been provided in the metal strip 760 so that the plasma generation might be intermittently interrupted (pulsed) if necessary to cool the subject material.

In another arrangement, the mesh might be placed in a stationary configuration (e.g., hung) above a moving conveyor belt with the contents of the belt being exposed to the plasma radicles as the contents pass underneath the mesh.

In summary, various embodiments utilize a conductive material insulated with a dielectric material. The conductive material could be metal but it need not be. Other materials include conductive fluids such as salt water, conductive electrolytes, or even a liquid metal such as mercury, etc. In application, the dielectric thread might be used to close wounds (e.g., used to suture a wound), disinfect powders, etc., as has been generally discussed previously.

In addition to using the instant dielectric thread as a strand or braided strand, it can also be woven into a mesh. The mesh can then be configured with a pore size that suits the particular application, e.g., whether powders, seeds, grains, or other granular objects are to be bulk sterilized. Additionally, and as has been discussed previously, according to an embodiment the plasma generation will not be only at the junctions of the strands as in the prior art, but instead plasma will be generated along the entire length of the strands that are woven together into the mesh.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

For purposes of the instant disclosure, the term "at least" followed by a number is used herein to denote the start of a range beginning with that number (which may be a ranger having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Terms of approximation (e.g., "about", "substantially", "approximately", etc.) should be interpreted according to their ordinary and customary meanings as used in the associated art unless indicated otherwise. Absent a specific definition and absent ordinary and customary usage in the associated art, such terms should be interpreted to be ±10% of the base value.

When, in this document, a range is given as "(a first number) to (a second number)" or "(a first number)-(a second number)", this means a range whose lower limit is the first number and whose upper limit is the second number. For example, 25 to 100 should be interpreted to mean a range whose lower limit is 25 and whose upper limit is 100. Additionally, it should be noted that where a range is given, every possible subrange or interval within that range is also specifically intended unless the context indicates to the contrary. For example, if the specification indicates a range of 25 to 100 such range is also intended to include subranges such as 26-100, 27-100, etc., 25-99, 25-98, etc., as well as any other possible combination of lower and upper values within the stated range, e.g., 33-47, 60-97, 41-45, 28-96, etc. Note that integer range values have been used in this paragraph for purposes of illustration only and decimal and fractional values (e.g., 46.7-91.3) should also be understood to be intended as possible subrange endpoints unless specifically excluded.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Further, it should be noted that terms of approximation (e.g., "about", "substantially", "approximately", etc.) are to be interpreted according to their ordinary and customary meanings as used in the associated art unless indicated otherwise herein. Absent a specific definition within this disclosure, and absent ordinary and customary usage in the associated art, such terms should be interpreted to be plus or minus 10% of the base value.

Still further, additional aspects of the instant invention may be found in one or more appendices attached hereto and/or filed herewith, the disclosures of which are incorporated herein by reference as if fully set out at this point.

Thus, the present invention is well adapted to carry out the objects and attain the ends and advantages mentioned above as well as those inherent therein. While the inventive device has been described and illustrated herein by reference to certain preferred embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

What is claimed is:

1. An apparatus for treating a subject with plasma radicles, comprising:
   (a) a first tubular member constructed of a dielectric material and having a first interior, said first tubular member containing a positive electrode in said first interior, said first tubular member having a first inlet and a first outlet for receiving and discharging fluid from an interior of said first tubular member; and,
   (b) a second tubular member constructed of said dielectric material having a second interior and situated proximate to said first tubular member, said second tubular member containing a negative electrode in said second interior, said second tubular member having a second inlet and a second outlet for receiving and discharging fluid from an interior of said second tubular member.

2. The apparatus for treating the subject with plasma radicles according to claim 1, further comprising:
   (c) a power source in electrical communication with said positive electrode of said first tubular member and said negative electrode of said second tubular member;
   (d) a first pump in fluid communication with said first tubular member interior; and,
   (e) a second pump in fluid communication with said second tubular member interior.

3. The apparatus for treating the subject with plasma radicles according to claim 1, wherein said positive electrode and said negative electrode are each an electrolytic solution.

4. The apparatus for treating the subject with plasma radicles according to claim 3, wherein said electrolytic solution is salt water.

5. The apparatus for treating the subject with plasma radicles according to claim 1, wherein said dielectric material is selected from the group consisting of polytetrafluoroethylene (PTFE), low density polyethylene (LDPE), and plastic.

6. An apparatus for treating a subject with plasma radicles, comprising:
   (a) a Peltier module,
   (b) a first tubular member constructed of a dielectric material and having a first interior, said first tubular member containing a positive electrode in said first interior, said first tubular member electrode being in thermal communication with said Peltier module; and,
   (c) a second tubular member constructed of said dielectric material having a second interior and situated proximate to said first tubular member, said second tubular member containing a negative electrode in said second interior, said second tubular member being in thermal communication with said Peltier module.

\* \* \* \* \*